United States Patent [19]

Diop et al.

[11] Patent Number: 5,389,686
[45] Date of Patent: Feb. 14, 1995

[54] ANALGESIC PROPERTIES OF FEDOTOZINE

[75] Inventors: Laurent Diop, Saclay; Agnés Grouhel, Meudon; Jean-Louis Junien, Sevres; Annick Langlois, Boulogne; Xavier Pascaud, Paris, all of France

[73] Assignee: Jouveinal SA, Fresnes Cedex, France

[21] Appl. No.: 91,691

[22] Filed: Jul. 13, 1993

Related U.S. Application Data

[63] Continuation of Ser. No. 37,966, Mar. 26, 1993, abandoned, which is a continuation-in-part of Ser. No. 937,127, Aug. 31, 1992, and Ser. No. 931,957, Aug. 19, 1992, Pat. No. 5,245,080, which is a continuation of Ser. No. 367,603, Jun. 19, 1989, abandoned.

[30] Foreign Application Priority Data

Feb. 20, 1989 [FR] France .................... 89 02177

[51] Int. Cl.$^6$ ............................ A61K 31/135
[52] U.S. Cl. ........................ 514/651; 514/649
[58] Field of Search ................ 514/651, 649

[56] References Cited

FOREIGN PATENT DOCUMENTS 384088 8/1990 European Pat. Off. .

OTHER PUBLICATIONS

Pascaud et al., Effects of Fedotozine on Gastrointestinal Motility in Dogs: Mechanism of Action and Related Pharmacokinetics, J. Pharm. Pharmacol. 42:546–552 (1990).
Bost et al., Effect of Fedotozine on Esophageal Motility in Healthy Volunteers Eur. J. Gastroenterol Hepatol, vol. 3 Suppl. 1 p. S-13 (1991).
Homerin et al., Efficacy of Fedotozine in Non-ulcer Dyspepsia, in World Congress of Gastroenterology, Sydney, 26–31 Aug., (1990) Abingdon: The Medicine Group (UK) Ltd., Abstract p. 455.
Karaus et al., Effect of Fedotozine on Postprandial Intestinal Motility and Orocecal Transit Time in Humans, J. Gastrointest. Motil. Vol 3 No. 3, 186 (1991).
Coffin et al., Fedotozine Increases Threshold of Discomfort to Gastric Distension in Healthy Subjects; Gastoenterology, 102,4 (1992) p. A437.
Freye, Opioid Agonists, Antagonists and Mixed Narcotic Analgesics; Drugs of Today, U. 25 No. 11 (1989) pp. 741–754.
Koster et al., Acetic Acid for Analgesic Screening, Fed. Proc. 18, p. 412 (1959).
Bentley et al., Br. J. Pharm. 73 (1981) pp. 325–332.
Hughes et al. Neuropeptides, Arzneim-Forsch Aug. Res., 42(1) Nr. 2a (1992) pp. 250–255.
Horwell, Kappa Opioid Analgesics, Drugs of the Future, 13 No. 12 pp. 1061–1071 (1988).
Costello et al., A Novel Series of Potent and Selective Agonists at the Opiod K–receptor, Euro. J. Pharm. 151 (1988) 475–48).
Kappa Agonists Making Progress as Novel Analgesics, SCRIP, No. 1697, (Mar. 4, 1992) p. 22.
B. Coffin et al., Effets de la fedotozine sur la sensibilite gastrique evalues par le barostat electronique chez l'homme sain, Gastroenterol. Clin. Biol. 16, A31 (Mar. 1992).
J. R. Malagelada, Am J. Physiol., 248 G229–237 (1985).

*Primary Examiner*—Marianne M. Cintins
*Assistant Examiner*—William R. A. Jarvis
*Attorney, Agent, or Firm*—Pennie & Edmonds

[57] ABSTRACT

Process for the treatment of painful syndromes, especially local and/or visceral, consisting in the parenteral or topical administration of a therapeutically effective quantity of the (−) tartrate of (+)-(R)-1-[(3,4,5-trimethoxy)benzyloxymethyl]-1-phenyl-N,N-dimethyl-n-propylamine.

13 Claims, No Drawings

ANALGESIC PROPERTIES OF FEDOTOZINE

This application is a continuation of application Ser. No. 08/037,966, filed Mar. 26, 1993, now abandoned, which is a continuation-in-part of application Ser. No. 07/937,127, filed Aug. 31, 1992, and a continuation-in-part of application Ser. No. 07/931,957, filed Aug. 19, 1992, now U.S. Pat. No. 07/367,603, filed Jun. 19, 1989, abandoned.

The present invention concerns analgesics in particular, the application of fedotozine (−) tartrate in the treatment of syndromes of painful hypersensitivity.

BACKGROUND OF THE INVENTION

Fedotozine (prop. INNM) is (+) (R)-1-[(3,4,5-trimethoxy)benzyloxymethyl]-1-phenyl-N, N-dimethyl-n-propylamine which, when salified with (2s, 3s)−(−) tartaric acid, is represented by the formula below:

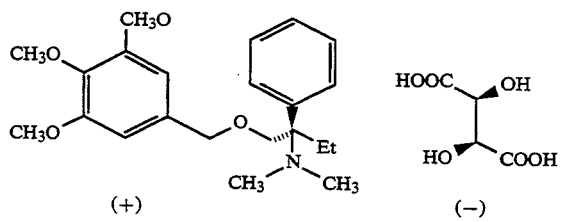

The compound modifies the digestive motilities, acting by a mechanism that involves the peripheral opiate receptors, notably those of the kappa ($\kappa$) type.

In European patent application No 0 384 088 it is shown that in vitro, the product shows a non-specific affinity for the opioid receptors, especially those of the mu and the kappa types. In vivo in mice it shows almost no analgesic effect when administered orally in the "writhing test" carried out as described by Koster. When administered orally to dogs it is found to stimulate the gastric drainage, and this led to the proposal that it should be used in man for the same application and to regularize the gastro-intestinal transits.

Furthermore, X. Pascaud et al. (J. Pharm. Pharmacol. 1990, 42: 546–62) have shown that apart from its stimulant activity at the level of the gastric antrum, in dogs the compound also has a stimulant action at the level of the small intestine and the colon.

These properties have been applied or proposed in man for the treatment of motility dysfunctions at various levels of the tract such as the gastro-oesophagal reflux (Bost, R. et al., Eur. J. Gastroenterol. Hepatol/1991, 3, S 13), dyspeptic conditions (Homerin, M. et al., World Cong. Gastroenterol. [Aug. 26–31, Sydney] 1190, Abst. PP 455) and motor atonicity of the small intestine (Karaus, M. et al., J; Gastrointest. Motil. 1991, 3: A186).

More recently, the present applicant has shown that when fedotozine (−) tartrate is administered to rats via the intravenous (i.v.) or subcutaneous (s.c.) routes, it restores the tonus and motility in an experimental adynamic ileus at the gastric and jejunal levels, and globally throughout the gastrointestinal tract. This use is disclosed in U.S. patent application Ser. No. 07/937,127, filed Aug. 31, 1992.

Finally, using healthy volunteers and a clinical-pharmacological model close to the latter symptomatology, which consisted in inducing a pseudo-obstructive distention at the gasric level, B. Coffin et al. (Gastroenterology, 1992, 102, 4, Apr., A437) found that (−) fedotozine tartrate reduced the sensation of discomfort in the subjects.

It is generally accepted that analgesic compounds are symptomatic medicaments that reduce or abolish painful sensations but without acting on the algogenic phenomenon, whose nature can vary (inflammation, muscular or visceral spasm, focus of infection, cancer, etc.) and can be of central or peripheral origin. Among such compounds the agonistic opiates, of which morphine is a typical representative, have known effects. Since the studies of Martin, who in 1976, under the heading of the opioid receptor class identified three types known as mu ($\mu$), delta ($\delta$) and kappa ($\kappa$), a very large number of investigations have attempted to define the roles and the respective involvements of those receptors in the physiology of life, and to prepare new agonistic or antagonistic ligands for them. In particular, one aim of research has been to prepare new compounds with analgesic activity of a power comparable with that of morphine, but exempt from its addictive side effects. To this end, numerous compounds showing affinity and marked selectivity for the various opioid receptors have been designed and synthesized. The most remarkable among these are agonistic and/or antagonistic $\mu$ and $\kappa$ receptor ligands, and these have been proposed for the treatment of various painful conditions as described in a review of the subject by E. Freye (Drugs of Today, Vol. 25, No 11, 1989, pp. 741–754).

On examining the pharmacological and clinical side effects of these compounds, it became apparent and established that apart from their analgesic action the $\mu$ agonists induce states of euphoria, a slowing-down of the gastro-intestinal transit, respiratory depression, habituation and addictive physical dependence, whereas with the $\kappa$ agonists the phenomena observed were essentially sedation, tolerance and diuretic effects, phenomena regarded as less serious than those induced by the $\mu$ agonists.

This consideration has motivated special interest in the search for $\kappa$-agonist analgesics, with efforts to improve them and to minimise their mainly sedative and diuretic side effects. The state of this work was reported in 1988 by David C. Horwell (Drugs of the Future, Vol. 13, No 12, 1988, pp. 1061–1071).

At present the $\kappa$ agonists are still considered to represent a step forward in the treatment of pain (SCRIP, No 1697, 1992, p. 22). Thus, they are regarded by some as the first new class of analgesics developed for many years.

In contrast to the majority of opioid analgesics developed, which are not selective and interact with the $\mu$ or $\delta$ receptors that probably mediate undesirable effects, it was hoped that specific $\kappa$ agonists would be exempt from these effects, especially the addictive ones. However, the compounds obtained so far only partially respond to that aim. In fact, all of them, to varying extents, show the familiar disadvantages, namely sedative and diuretic effects, the latter in particular having been observed in clinical trials or pharmacological studies with compounds considered to be reference $\kappa$ agonists such as U-50,488H and PD-117302 that are representative of the chemical category of arylacetamides.

Similarly, the development of certain products that are less selective towards the $\kappa$ receptors, such as bremazocine, was interrupted because of their capacity to induce modifications of the mental condition or behavioural changes.

Recently, J. Hughes and G. N. Woodruff have reviewed the state of the subject ("Neuropeptides", Arzneim.-Forsch. 42 (6) 2a (1992), p. 250). They state that for a long time there has been considerable interest in the possibility of inducing analgesia via the κ receptors as an alternative solution to treatment via the type-μ opiates. The κ receptors are localized at the sites concerned with the process and transmission of nociceptive information (substantia gelatinosa, thalamus, periaqueductal grey matter, -monoaminergic neurons). In tests carried out with animals the κ agonists are antinociceptive agents and are more effective against the reflexes induced by pressure and chemical stimuli than by the tests provoked by heat (Przelocki 1987). They are particularly effective against inflammatory pains (Haley et al. 1990).

Apart from the potential reduction of tolerance and physical dependence risks, the κ agonists have the advantage of inducing only minimum respiratory depression and having no constipatory effects. However, all compounds of this category tested in man have induced a range of subjective effects (Horwell 1988) and, at the present state of research, none of those studies has succeeded in discovering a κ-agonist compound that is truly selective and that possesses a large enough margin between the analgesic effect sought and the undesirable side effects, whether subjective or objective, the most evident of which are the sedative and diuretic effects.

SUMMARY OF THE INVENTION

In a breakthrough from this state of the art, it has just been found that fedotozine (−) tartrate, previously regarded as a modifier of the digestive motilities when administered orally, unexpectedly shows a peripheral analgesic action when administered via the parenteral route exempt from any of the sedative, hypotensive, respiratory-depressive, dysphoric or diuretic effects usually encountered with this class of compounds.

In accordance with a mode of action never before encountered with an analgesic, the present invention makes it possible to treat painful peripheral syndromes by the peripheral or local administration of a composition containing a therapeutically effective quantity of fedotozine (−) tartrate (prop. INNM), namely the (−) tartrate of (+) (R)-1-[(3,4,5-trimethoxy)-benzyloxymethyl]-1-phenyl-N,N-dimethyl-n-propylamine.

For this purpose the invention envisages a process for manufacturing an analgesic medicament, which consists in mixing (−) fedotozine tartrate with an excipient, for administration via the local or peripheral routes.

A second aspect of the invention envisages a pharmaceutical composition intended to reduce and/or suppress painful symptoms, in particular those induced by conditions of hypersensitivity or hyperreactivity, characterized in that it contains a therapeutically effective quantity of fedotozine (−) tartrate and an excipient that is suitable for topical administration.

DETAILED DESCRIPTION OF THE INVENTION

As shown by the pharmacological studies reported below, it has been established that the action mechanism of the product involves its agonist affinity for the peripheral opioid receptors at the sensorial nerve ends, in relation to the effects induced by a painful stimulus to a tissue with normal sensitivity threshold. In a particularly surprising way, this action mechanism, which operates during a stimulus to a hypersensitive or hyperreactive tissue whose sensitivity threshold is reduced, involves the affinity of fedotozine (−) tartrate for the population of receptors specifically involved in the phenomenon of pain, which seem to be the κ receptors since this analgesic action is inhibited by nor-BNI which is known to have an antagonistic affinity for the κ receptors. As reported in European application No 0 384 088, the respective affinities of (−) fedotozine tartrate for the μ, δ and κ receptors are 196, 540 and 232, expressed as their nanomolar 50% inhibiting concentrations ($IC_{50}$), i.e. essentially of the same order for the μ and κ receptors. Bearing this in mind, the pharmacological studies intended to detect and then elucidate the mode of analgesic action of the product of this invention were carried out by comparison with morphine, as a representative of the μ agonist compounds, and with the compound recognised as one of the most selective with a κ agonist affinity (Eur. 3. Pharm. 151, 1988, pp. 475–478), coded as U-50,488H, namely trans-3,4-dichloro-N-(methyl) -N-[2-(1-pyrrolidinyl)-cyclohexyl]-benzeneacetamide in the form of its addition salt with methanesulphonic acid.

In addition, naloxone and norbinaltorphimine: nor-BNI (Porthogese et al. 1987), which are respectively antagonistic ligands specific to the μ and κ receptors, were included in some of the studies.

The pharmacological tests carried out to demonstrate the analgesic properties of fedotozine (−) tartrate consisted in the first instance in determining the analgesic effect on pain induced by nociceptive mechanical, thermal or chemical stimuli at sites of sensivity regarded as normal, and then, in a second stage, in studying the analgesic effect on pain induced by a nociceptive mechanical stimulus at a site previously hypersensitized by chemical irritation.

In conformity with the known properties of κ-agonist compounds, the compound was found inactive when administered orally to rats to counteract a nociceptive thermal stimulus applied in a condition of normal sensitivity (tail-flick test, dose >200 mg/kg). In contrast, it showed analgesic effects in local painful conditions induced by the topical administration of a chemical agent, namely acetic acid administered via the intraperitoneal route in Koster's test and in the same test as modified by Bentley.

In addition, the product shows an analgesic action against painful conditions induced by mechanical distention in the colonic mucosa in rats.

As for the peripheral analgesic activity in situations of hypersensitivity and hyperreactivity, the test consists in first inducing a local irritation with acetic acid, and then provoking the pain by mechanical distention identical to that carried out in the previous test.

The results, which are presented in detail in the descriptive section that follows, show that (−) fedotozine tartrate inhibits the pain induced by i.p. injection of acetic acid when administered locally ($ED_{50}$ 3.23 mg/kg - test according to Bentley), whereas it has little or no effect when administered p.o. or s.c. (17.6% of analgesia at 50 mg/kg p.o. and $ED_{50}=26.1$ mg/kg s.c. - test according to Koster). These results should be compared against those obtained with morphine and with U-50,488H, both of which have marked activity p.o. and are nearly 25 times more active than the compound of the invention via the s.c. route. Quite clearly, the analgesic action of (−) fedotozine tartrate occurs essentially locally, in contrast to the comparison products which are known to be very active via the customary general routes.

The test, which consists in inducing pain by distending the normal colonic mucosa in a rat, shows that in contrast to morphine and U-50,488H, which are also active via the central route (intracerebroventricular), fedotozine (−) tartrate is only active via the i.v. route. Surprisingly, when the same test is applied to colonic mucosa previously sensitized by acetic acid, it is found that under these conditions the product is more active than on normal mucosa, and that its action mechanism involves its interaction with the receptors specifically implicated in the nociceptive phenomenon. Thus, in contrast to morphine and to the compound U-50,488H, which have analgesic effects at identical doses whether the mucosa be normal or hypersensitized, fedotozine (−) tartrate is found to be over twice as active on the sensitized colonic mucosa than on the normal mucosa and, in a way that is specific to itself, its activity then implicates a population of receptors that seems to be revealed by the state of hypersensitization; receptors that seem to be of type $\kappa$ since under these conditions the analgesic effect is wholly inhibited by the antagonist nor-BNI.

These tests demonstrate the particular activity of fedotozine (−) tartrate which, in nociceptive processes induced under conditions of normal sensitivity, shows a local and/or peripheral analgesic action and which, in nociceptive processes induced under conditions of hypersensitivity, seems to act specifically on the k-type receptors which are revealed or differentiated under such conditions.

Moreover, the pharmacological effects of the product are not accompanied by any of the sedative, hypotensive, respiratory-depressant, dysphoric or diuretic effects generally encountered with this class of compounds.

The tests carried out to demonstrate the above properties are reported in the experimental section below.

EXAMPLES

A) Analgesic action via the local route

Principle of the test

The test consists in injecting mice with a solution of acetic acid via the intraperitoneal route. The animal twists its body around, especially the abdominal wall which undergoes contractions, whence the name "writhing test" commonly used for this test.

In the version proposed by R. Koster (Fed. Proc. 1959, 18, p. 412) the test products are administered orally ten minutes before the i.p. injection of the acetic acid solution. A modification proposed by G. A. Bentley (Br. J. Pharm. 1981, 73, pp. 325-332) consists in administering the test product via the i.p. route a few minutes after the administration of the acid solution. This modification shows up the immediate local antinociceptive action of the compounds.

Experiments

In the test carried out by the method proposed by G. A. Bentley, male mice weighing 22±2 g are used. The animals are divided into groups of six animals per cage.

The animals receive via the intraperitoneal (i.p.) route 0.1 ml per 10 g of body-weight of a 0.6% acetic acid solution in distilled water kept at 37° C. The test compounds are administered via the i.p. route six minutes after the acetic acid, dissolved in distilled water and in a volume of 0.1 ml per 20 g of body-weight.

Immediately after this administration the animals are transferred into individual cages. The number of abdominal cramps manifested by each animal is counted during a period of 5 minutes, from the second to the seventh minute after the injection of the test product. For each group, the average number of cramps and its standard deviation are calculated.

The percentage activity for each dose administered is calculated and compared with the control group, and the results are expressed as an $ED_{50}$, namely the dose required to inhibit 50% of the abdominal cramps induced by the administration of acetic acid under the conditions of the experiment.

Results

The table below shows the results obtained with (−) fedotozine tartrate, morphine and the compound U-50,488H, these products being administered either via the p.o. and s.c. routes in the test according to Koster, or via the i.p. route in the test according to Bentley.

|  | Test according to BENTLEY | Test according to KOSTER | |
|---|---|---|---|
|  | i.p. route | s.c. route | p.o. route |
| FEDOTOZINE (−) TARTRATE | $ED_{50}$ = 3.23 mg/kg | $ED_{50}$ = 26.10 mg/kg | 17.6% for 50 mg/kg |
| MORPHINE | $ED_{50}$ = 0.33 mg/kg | $ED_{50}$ = 0.70 mg/kg | 78% for 10 mg/kg |
| U-50,488H | — | $ED_{50}$ = 1.1* mg/kg | 90% for 50 mg/kg |

Apart from the virtual inactivity of fedotozine (−) tartrate p.o. in the Koster test, these results show convingly that the activity of the product is almost exlcusively local, considering that its analgesic action is nearly 10 times weaker via the s.c. route than via the i.p. route. With morphine the s.c. activity is only half as much as the i.p. activity, in agreement with the fact that morphine acts both via the general route and via the local route. Considering these ratios, the specificity of the local action of fedotozine (−) tartrate is seen to be about five times greater than that of morphine.

B) Antinociceptive effect on the visceral pain induced by distention of the hypersensitized colon in rats Principle of the test The aim of the test is to evaluate the antinociceptive action of FZ after sensitization of the colonic mucosa in rats by an irritation induced chemically using acetic acid (AA).

Experiments

The colonic sensitization is induced by intrarectal injection of acetic acid (0.6% w/v, 1 ml/rat) (AA), 30 min before the application of successive colonic distentions effected by blowing up a balloon (75 mmHg, 30 sec). By reflex action, this induces a hypotension of reproducible intensity in male Sprague-Dawley rats (340–360 g) anaesthetized with sodium pentobarbital (60 mg/kg i.p.). The arterial pressure is recorded via a carotid catheter. The treatments take place via the intravenous route after 3 or 4 controlled responses.

Results

Acetic acid (AA) induces a reduction of the distention threshold (AA: 6 mmHg; controls: 14 mmHg), an increase in the amplitude of the cardiovascular response (+71.9%, p <0.05), associated with histological effects in the mucosa consisting in congestion and superficial haemorrhage. Under these conditions of colonic mucosa sensitization, fedotozine (−) tartrate is found to be over twice as active after AA irritation [$ED_{50}=1.15$ mg/kg (0.85–1.57)] than in the control rats not subjected to the preliminary irritation [$ED_{50}=2.57$ mg/kg (1.68–4.11)]. The specific κ-receptor antagonist nor-BNI (10 mg.kg, s.c. route) wholly inhibits the action of the product observed after sensitization. The antinociceptive profiles of the sensitized rats compared with the control rats are not changed by AA irritation either in the case of morphine or in that of U-50,488H [morphine: $ED_{50}=0.33$ mg/kg (0.28–0.39) versus 0.31 mg/kg (0.24–0.41); U-50,488H: $ED_{50}=0.31$ mg/kg (0.29–0.33) versus 0.33 mg/kg (0.15 - 0.71)]. These results demonstrate the preponderance of the κ receptors in this model of pain induced in an area considered to correspond to an inflammatory condition or a tissue aggression. The astonishing specificity of the product's activity compared with that of the compound U-50,488H suggests that κ receptors are revealed or activated, for which the two substances have differentiated activities. In other words, during this test, by reaction to mechanical stimuli applied to a hypersensitized colon, it seems that one is bringing to light a sub-category of κ receptors that are recognized preferentially by fedotozine (−) tartrate but not by the κ agonist U-50,488H.

The pharmacological properties mentioned above demonstrate the utility of fedotozine (−) tartrate in treatments via the peripheral routes of local and especially visceral pains of various aetiologies.

The compositions conforming to the invention can be used to inhibit painful attacks of hepatic colic, or abdominal pain induced by radiological examinations such as colonoscopies. They are also useful in the treatment of pains that are part of symptomatologies such as colopathies, post-operative conditions, or even visceral pains associated with cancerous conditions.

For the application of the properties just described, one aspect of the invention concerns a pharmaceutical composition intended to reduce and/or suppress painful symptoms, notably those induced in conditions of hypersensitivity or hyperactivity, characterized in that it contains a therapeutically effective quantity of fedotozine (−) tartrate.

To prepare these compositions the compound is used at a level of purity compatible with pharmaceutical utilization, namely higher than 95% as described in the preparation processes specified in European patent application No 0 384 088.

The dose used to achieve the therapeutic effect desired is adapted to the nature and severity of the painful affection which, in some cases, such as the pain provoked by radiological examinations, can be treated preventively. For this purpose the compound is administered via parenteral routes other than the oral route, in the form of compositions compatible with, for example, the rectal, vaginal, topical, intravenous parenteral, or even intramuscular routes. Thus, suppositories or ovules can be used for the rectal and vaginal routes, lotions and creams for the topical routes, and aqueous solutions for the injectable forms or sprays. So far as the solid forms (suppositories, ovules) are concerned, these consist of 1 to 40% by weight of fedotozine (−) tartrate with a suitable excipient representing 99 to 60% by weight of the finished composition.

Compositions intended for injection are aqueous solutions or even unitary doses of the product in powdered form intended to be dissolved at the time of use in water of appropriate quality. Solutions of isotonic composition are proposed for administration by intravenous perfusion in units of 100 ml containing the active ingredient at a concentration of 0.001 to 1.0% by weight and more favourably 0.01 to 0.5% by weight of fedotozine (−) tartrate. The solutions are also proposed in unitary doses 1.0 to 10 ml in volume packaged in suitable ampoules, the solutions in those ampoules containing 0.1 to 5.0% by weight of the active ingredient and preferably 0.25 to 2.5%.

Depending on the nature and intensity of the painful condition to be treated, the daily dose will range from 5 to 1000 mg and more favourably from 25 to 500 mg of fedotozine (−) tartraten, and this can be divided into several separate administrations.

In treatments by injection, notably via the intravenous route, the doses of the product injected in a single bolus can be from 5 to 500 mg of the product without inducing any Serious undesirable effects, the most usual dose being 25 mg. By slow injection, the treatments currently administered consist of between one and four injections per day, each of 25 to 100 mg of fedotozine (−) tartrate, the most usual treatment being four times 50 mg of the product per day. As a non-limiting example, the composition and preparation of an isotonic injectable solution containing 0.1% of the active ingredient in a unitary dose of 5 ml are described below.

| Formulation | |
|---|---|
| Compounds for the preparation of 100 ml of solution: | |
| - (−) tartrate of (+)-(R)-1-[(3,4,5-trimethoxy) benzyloxymethyl]-1-phenyl-N,N-dimethyl-n-propylamine | 0.100 g |
| - officinal sodium chloride | 0.850 g |
| - distilled water for injectable preparations, up to | 100 ml |

Preparation

The compounds are dissolved in about 95% of the distilled water intended for the preparation, at a temperature close to 20° C. and with stirring. The solution obtained is filtered through a membrane of 22-micron porosity, and the filtrate is then made up to the exact volume with distilled water that has also been filtered. The solution is packaged in ampoules containing 5 ml each, which are then sealed and sterilized at 121° C. for 30 min.

We claim:

1. A method for the treatment of hypersensitivity to pain, which comprises administering to a subject in need of such treatment a therapeutically effective amount of the compound fedotozine (−) tartrate.

2. The method according to claim 1, wherein a dose of about 5 to 1000 mg of fedotozine (−) tartrate is administered.

3. The method according to claim 1, wherein the compound is administered parenterally.

4. The method according to claim 1, wherein the compound is administered in a composition in the form of suppositories, ovules, lotions, creams or aqueous solutions.

5. The method according to claim 4, wherein the aqueous solutions are administered by perfusion via the i.v. route and contain about 0.01 to 0.5% w/v of (—) fedotozine tartrate.

6. The method according to claim 4, wherein the aqueous solutions are administered by injection and contain about 0.25 to 2.5% by weight of fedotozine (—) tartrate.

7. The method according to claim 1 wherein the compound is at least twice as active upon pain induced during a physiological condition of hypersensitivity than upon pain induced during a normal physiological condition.

8. A method for treating pain and producing local analgesia which comprises administering to a subject in need of such treatment a therapeutically effective amount of the compound fedotozine (—) tartrate.

9. The method according to claim 8 wherein a dose of about 5 to 1000 mg of fedotozine (—) tartrate is administered.

10. The method according to claim 8 wherein the compound is administered parenterally.

11. The method according to claim 8 wherein the compound is administered in a composition in the form of suppositories, ovules, lotions, creams or aqueous solutions.

12. The method according to claim 11 wherein the aqueous solutions are administered by perfusion via the i.v. route and contain about 0.01 to 0.5% w/v of fedotozine (—) tartrate.

13. The method according to claim 11 wherein the aqueous solutions are administered by injection and contain about 0.25 to 2.5% by weight of fedotozine (—) tartrate.

* * * * *